United States Patent
Perego et al.

(10) Patent No.: US 7,154,015 B2
(45) Date of Patent: Dec. 26, 2006

(54) PROCESS FOR THE PRODUCTION OF PROPYLENE FROM OLEFINIC STREAMS

(75) Inventors: Carlo Perego, Carnate-Milan (IT); Stefano Peratello, Milan (IT); Paolo Pollesel, Milan (IT); Sergio Sgorlon, Campalto-Venezia (IT); Maria Angela Mantegazza, Monza-Milan (IT); Massimo Romagnoli, Milan (IT)

(73) Assignees: Enichem S.p.A., San Donato Milanese (IT); Enitecnologie S.p.A., San Donato Milanese (IT)

( * ) Notice: Subject to any disclaimer, the term of this patent is extended or adjusted under 35 U.S.C. 154(b) by 425 days.

(21) Appl. No.: 10/019,273

(22) PCT Filed: May 15, 2001

(86) PCT No.: PCT/EP01/05578

§ 371 (c)(1),
(2), (4) Date: Apr. 9, 2002

(87) PCT Pub. No.: WO01/90034

PCT Pub. Date: Nov. 29, 2001

(65) Prior Publication Data

US 2002/0175110 A1    Nov. 28, 2002

(30) Foreign Application Priority Data

May 19, 2000    (IT)    ............................ MI2000A1111

(51) Int. Cl.
*C07C 4/06*    (2006.01)
(52) U.S. Cl. ...................... 585/648; 585/651; 585/653; 208/120.01
(58) Field of Classification Search ................ 585/648, 585/651, 653; 208/120.01
See application file for complete search history.

(56) References Cited

U.S. PATENT DOCUMENTS

| | | | | |
|---|---|---|---|---|
| 3,832,449 A | * | 8/1974 | Rosinski et al. | ............ 423/705 |
| 5,026,936 A | * | 6/1991 | Leyshon et al. | ............ 585/315 |
| 6,069,287 A | * | 5/2000 | Ladwig et al. | ............... 585/648 |

FOREIGN PATENT DOCUMENTS

WO    99 29805    6/1999

* cited by examiner

*Primary Examiner*—Thuan D Dang
(74) *Attorney, Agent, or Firm*—Oblon, Spivak, McClelland, Maier & Neustadt, P.C.

(57) ABSTRACT

Process for the production of propylene starting from mixtures of hydrocarbons, prevalently olefins, the above hydrocarbons having a boiling point ranging from −15° C. to +80° C., preferably from −12° C. to +60° C., which comprises putting the above mixture of hydrocarbons in contact, under cracking conditions, with a large-pore zeolite having a molar ratio Silica/Alumina lower than 200, preferably ranging from 50 to 150.

18 Claims, 3 Drawing Sheets

Figure 1:
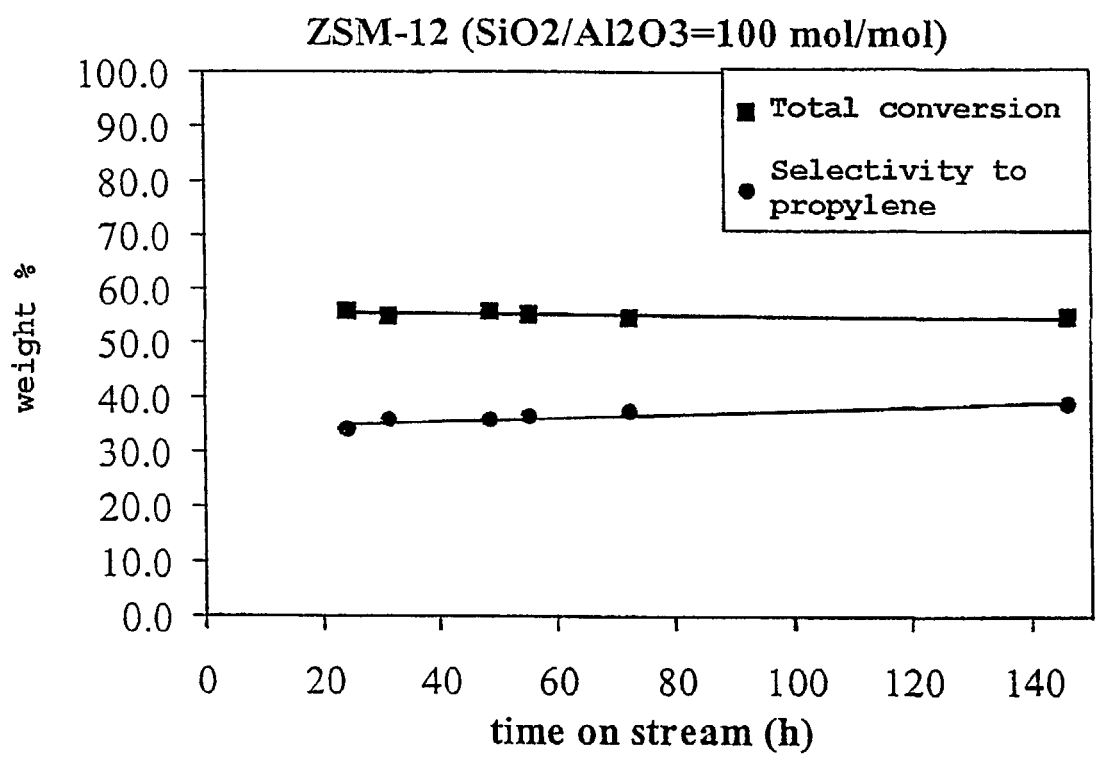

Curves relating to total conversion and selectivity to propylene, obtained with the catalyst ZSM-12 having a molar ratio $SiO_2/Al_2O_3 = 100$ in relation to the time on stream (h)

Curves relating to total conversion and selectivity to propylene, obtained with the catalyst ZSM-12 having a molar ratio $SiO_2/Al_2O_3 = 100$ in relation to the time on stream (h)

Curves relating to total conversion and selectivity to propylene, obtained with the catalyst ZSM-12 having a molar ratio $SiO_2/Al_2O_3 = 250$ in relation to the time on stream (h)

Curves relating to total conversion and selectivity to propylene, obtained with the commercial catalyst ZSM-5 (CBV 3020 E) in relation to the time on stream (h)

PROCESS FOR THE PRODUCTION OF PROPYLENE FROM OLEFINIC STREAMS

The present invention relates to a process for the production of propylene from prevalently olefinic hydrocarbon streams.

More specifically, the present invention relates to a selective cracking process for the production of propylene starting from mixtures of hydrocarbons, prevalently olefins, the above hydrocarbons having a boiling point ranging from −15° C. to +80° C., preferably from −12° C. to +60° C.

A typical example of these fractions are essentially $C_4$–$C_6$ fractions coming from steam cracking and catalytic cracking, having an olefin content of at least 40% by weight, usually at least 70% by weight.

Propylene is one of the most important chemical products from the point of view of demand and production volume and is mainly used in the production of polymers. The main propylene source is the steam cracking process, in which hydrocarbon charges with a high paraffin content are thermally treated in the presence of vapour. The main products of steam cracking are propylene and ethylene, which leave the process in a ratio of about 0.5. As the market request for propylene has become greater in the last few years with respect to that of ethylene and owing to the fact that the propylene/ethylene ratio cannot be significantly varied, it has become necessary to increase the production of propylene using alternative methods. In fact, in 1999 there was a considerable deficit of propylene in Western Europe, with importations of this product amounting to 195,000 tons. The production of large quantities of propylene by means of processes which appropriately treat steam cracking by-products can allow variations in the overall propylene/ethylene ratio, thus meeting market demands. The possibility of having flexible processes allowing a certain flexibility in the propylene/ethylene ratio would therefore provide great economic advantages.

An interesting possibility consists in a selective catalytic cracking process which converts $C_4$–$C_5$ fractions to propylene. The fractions can derive from steam cracking but it is also possible to extend the process to other similar streams coming for example from FCC (Fluid Catalytic Cracking). The charges can also derive from the above fractions after extraction and/or enrichment in olefins.

The use of solid acid catalysts, among which amorphous silico-aluminas and in particular zeolites, in the cracking reaction of hydrocarbons, is known in literature (see for example J. Scherzer, Cata. Rev.—Sci. Eng., 31(3), 215–354, 1989).

The most important application of these materials in cracking reactions, from an industrial point of view, is that called FCC (Fluid Catalytic Cracking) whose purpose, starting from heavy charges such as vacuum gas oils, is to produce lighter hydrocarbon cuts, particularly within the boiling range of gasolines. The catalysts currently used in this process are Y-type zeolites (IUPAC abbreviation: FAU) containing various additives.

A different type of cracking, owing to the charges used and type of products to be obtained, is called "selective cracking". The purpose of "selective cracking" is to produce light olefins, such as ethylene and propylene, starting from $C_4$–$C_6$ hydrocarbon fractions and therefore already light, if compared to a vacuum gas oil. The advantage of this process consists in transforming low quality hydrocarbon fractions, difficult to distribute on the market, to olefins having a higher added value.

Various zeolitic materials active in "selective cracking" reactions, are described in literature. For example, EP-A-109,059 and EP-A-109,060 describe the use of ZSM-5 zeolite (IUPAC abbreviation: MFI) for selective cracking reactions. These documents demonstrate that the best catalytic performances, referring to yields to propylene and ethylene, are obtained when the $SiO_2/Al_2O_3$ ratio of the zeolite is high. More specifically, EP-A-109,059 claims, for MFI-type zeolites (ZSM-5) $SiO_2/Al_2O_3$ ratios lower than or equal to 300 (mol/mol), preferably between 25 and 220, whereas EP-A-109,060 discloses $SiO_2/Al_2O_3$ ratios higher than or equal to 350 (mol/mol).

WO 99/57226 describes a method for converting hydrocarbon charges, with a boiling point within the naphtha range, to propylene in the presence of medium-pore zeolites having an $SiO_2/Al_2O_3$ ratio greater than 200 (mol/mol). The above document provides two experimental examples: in the first, three medium-pore zeolites ZSM-48 ($SiO_2/Al_2O_3>1500$), ZSM-22 ($SiO_2/Al_2O_3>1500$) and ZSM-5 ($SiO_2/Al_2O_3=55$) are compared. It is shown that the selectivity to propylene for the first two catalysts is higher with respect to ZSM-5. In the second example, two ZSM-22 zeolites having a different $SiO_2/Al_2O_3$ ratio (>1500 and 120) are compared. It is shown that the one with the greater $SiO_2/Al_2O_3$ ratio has the higher selectivity to propylene.

Finally, WO 99/29805 describes a process for producing propylene starting from $C_4$ and higher olefinic streams, in the presence of MFI zeolite (ZSM-5) having an $SiO_2/Al_2O_3$ ratio of at least 180 (mol/mol).

Experts in the field, however, still feel the necessity for using materials suitable for obtaining greater conversions and at the same time having a higher stability of the catalytic activity over a period of time. An extremely important problem, in fact, which is not taken much into consideration in literature, consists in the poor stability of the catalytic material over a period of time.

A process has now been found, which uses materials capable of improving the yield to propylene and that also have the great advantage of maintaining the catalytic performances practically constant over a period of time.

In accordance with this, the present invention relates to a process for the production of propylene starting from mixtures of hydrocarbons, prevalently olefins, the above hydrocarbons having a boiling point ranging from −15° C. to +80° C., preferably from −12° C. to +60° C., which comprises putting the above mixture of hydrocarbons in contact, under cracking conditions, with a large-pore zeolite having a molar ratio Silica/Alumina lower than 200, preferably ranging from 50 to 150.

The hydrocarbon mixtures essentially consist of hydrocarbons, both olefins and paraffins, having a boiling point ranging from −15° C. to +80° C., preferably from −12° C. to +60° C. Typical examples of hydrocarbons forming the above hydrocarbon mixtures are 1-butene, trans-2-butene, cis-2-butene, n-butane, isobutane, propane, pentane, isopentane, 1-pentene, 2-pentene, n-hexane, 1-hexene, 2-hexene. The hydrocarbon mixtures comprise from 30% to 100% by weight of olefins, preferably from 40% to 85% by weight. The paraffins contained in the hydrocarbon mixtures range from 5% to 65% by weight, preferably from 10% to 50% by weight, even more preferably from 20% to 45% by weight.

The term "cracking conditions" refers to a temperature at which the contact between the hydrocarbon mixtures and catalyst takes place, ranging from 400° C. to 750° C., preferably from 450° C. to 700° C., even more preferably from 500° C. to 650° C.

The process of the present invention is preferably carried out at a weight hourly space velocity (WHSV) ranging from $0.1\ h^{-1}$ to $1,000\ h^{-1}$, more preferably from $0.5\ h^{-1}$ to $100\ h^{-1}$, even more preferably from $0.8\ h^{-1}$ to $50\ h^{-1}$.

The pressure in the contact zone between catalyst and hydrocarbon mixtures ranges from 0.1 to 30 absolute atm., preferably from 1 to 3 absolute atm., more preferably about 1 absolute atm.

The process of the present invention can be carried out using any reactor solution, for example, fixed bed, moving bed, a "riser" reactor or a fluid bed, preferably fixed bed.

The catalyst which can be used in the process of the present invention is a large-pore zeolite having a molar ratio Silica/Alumina lower than 200, preferably ranging from 50 to 150. The term "large-pore zeolite" refers (see N. Y. Chen and T. F. Degnan, Chemcial Engineering Progress, February 1988, 32–41) to a zeolite have a lattice consisting of 12 tetrahedrons. The above zeolite has a molar ratio Silica/Alumina lower than 200, preferably ranging from 50 to 150. In the preferred embodiment, the zeolite is ZSM-12 (IUPAC abbreviation: MTW), having a molar ratio Silica/Alumina lower than 200, preferably ranging from 50 to 150. The preparation of this zeolite is well known to experts in the field.

The zeolite can be used as such or mixed with inert products, in the form of granules or pellets.

Contrary to what is specified in scientific and patent literature, the ZSM-12 material has the best catalytic performances at $SiO_2/Al_2O_3$ ratios<200 (mol/mol). The best catalytic performances refer to both yields to propylene and stability (duration) of the catalyst over a period of time.

The following examples are provided for a better understanding of the present invention.

EXAMPLES

The catalytic testing experiments were carried out in a continuous laboratory plant, with a fixed bed tubular reactor configuration. The reaction products were characterized with a gaschromatograph model HP 5890 equipped with a "PONA" capillary column.

The synthetic mixture of $C_4$ hydrocarbons indicated in Table 1 was used for the experimental tests. This mixture has a similar composition to the stream called "Refined III" deriving from steam cracking.

TABLE 1

Mixture used in the catalytic tests

| Hydrocarbon | Feeding (weight %) |
| --- | --- |
| 1-butene | / |
| Trans-2-butene | 52.35 |
| Cis-2-butene | 24.86 |
| n-butane | 22.61 |
| Iso-butane | 0.18 |
| Sum of olefins | 77.21 |

The weight quantities of hydrogen, methane, ethane, ethylene, propane, propylene, n-butane, isobutane, 1-butene and isobutene, cis-2-butene, trans-2-butene, butadiene and a fraction of heavier products called $C_5^+$, were determined in the gaseous reaction products.

The catalyst was charged in a quantity varying from 2 to 10 g, in granules of 20–40 mesh or in pellets of 2–4 mm, mixed with corindone (inert product), in a weight ratio of 1:1.

Example 1

Synthesis of ZSM-12 ($SiO_2/Al_2O_3$=100 mol/mol)

2.4 g of sodium aluminate with a content of $Al_2O_3$ equal to 56% are added to an aqueous solution of tetramethylammonium hydroxide at 35%. The solution thus obtained is poured, under stirring, into 200 g of colloidal silica Ludox HS 40.

A limpid, homogeneous gel is obtained, which is poured into an AISI316 steel autoclave, equipped with an anchor stirrer. The gel is left to crystallize under hydrothermal conditions at 165° C. for 90 hours.

After cooling the autoclave, the solid obtained is separated from the mother liquor and washed with demineralized water until the washing water has a pH of less than 9.

The solid obtained is calcined at 550° C. in a stream of air for 5 hours.

The solid thus obtained is subjected to ionic exchange by means of suspension in an aqueous solution of ammonium acetate. The ammonium ion is present in excess with respect to the nominal aluminum present in the solid. After filtration and washing of the solid, the whole operation (exchange and washing) is repeated.

The solid obtained is calcined at 550° C. in a stream of air for 5 hours.

The zeolitic solid is thus obtained in its acid form which, upon XRD analysis reveals the presence of the sole crystalline phase of the ZSM-12 type (MTW). Chemical analysis shows a content of residual sodium of less than 50 ppm and a molar ratio $SiO_2/Al_2O_3$=100.

Comparative Example 2

Synthesis of ZSM-12 ($SiO_2/Al_2O_3$=250 mol/mol)

0.97 g of sodium aluminate with a content of $Al_2O_3$ equal to 56% are added to an aqueous solution of tetramethylammonium hydroxide at 35%. The solution thus obtained is poured, under stirring, into 200 g of colloidal silica Ludox HS 40.

A limpid, homogeneous gel is obtained, which is poured into an AISI316 steel autoclave, equipped with an anchor stirrer. The gel is left to crystallize under hydrothermal conditions at 165° C. for 90 hours.

After cooling the autoclave, the solid obtained is separated from the mother liquor and washed with demineralized water until the washing water has a pH of less than 9.

The solid obtained is calcined at 550° C. in a stream of air for 5 hours.

The solid thus obtained is subjected to ionic exchange by means of suspension in an aqueous solution of ammonium acetate. The ammonium ion is present in excess with respect to the nominal aluminum present in the solid. After filtration and washing of the solid, the whole operation (exchange and washing) is repeated.

The solid obtained is calcined at 550° C. in a stream of air for 5 hours.

The zeolitic solid is thus obtained in its acid form which, upon XRD analysis reveals the presence of the sole crystalline phase of the MTW type. Chemical analysis shows a content of residual sodium of less than 50 ppm and a molar ratio $SiO_2/Al_2O_3$=250.

Example 3

Catalytic test with ZSM-12 (SiO$_2$/Al$_2$O$_3$=100 mol/mol)

The catalytic testing of ZSM-12 zeolite having a molar ratio SiO$_2$/Al$_2$O$_3$=100 (example 1), was carried out using the equipment described above and under the following operating conditions:
Reaction T=500° C.;
Total pressure=1 bar;
WHSV$_{total}$=1 h$^{-1}$;
Feeding see Table 1.

The WHSV is defined as a ratio between the hourly weight flow-rate (g/h) of the mixture in the feeding divided by the weight of the catalyst (g). From a dimensional point of view it is h$^{-1}$.

FIG. 1 indicates the two curves relating to total conversion and selectivity to propylene, obtained with the catalyst ZSM-12 having a molar ratio SiO$_2$/Al$_2$O$_3$=100, in relation to the time on stream (tos).

The total conversion is defined as follows:

Tot. conv. %=[(C$_4$ at the reactor inlet)−(C$_4$ at the reactor outlet)]/(C$_4$ at the reactor inlet)·100.

In this way the C$_4$ fraction is not divided into olefins or paraffins but is considered altogether as a potential reagent.

The selectivity to propylene is calculated as:

selectivity to propylene%=(yield to propylene)/(total conversion)·100.

The yield to propylene is experimentally obtained by gaschromatographic analysis.

In addition to the high conversion and selectivity values, the unexpected stability of this material over a period of time is extremely important. In fact, it can be noted from the graph of FIG. 1 that no catalytic deterioration phenomena are present until at least 140 h of tos.

This stability over a period time makes the material particularly suitable for use in simple reactor conditions such as fixed beds.

More complicated solutions, however, such as fluidized/transported beds can obviously also be used.

Table 2 indicates, for illustrative purposes, the selectivity of the different components forming the product at the outlet of the plant. Among olefins of interest, ethylene is also present (7.88%). C$_5^+$ refers to the liquid fraction, at atmospheric pressure and room temperature, of the product leaving the plant. Owing to the high number of hydrocarbons present in the C$_5^+$ fraction, Table 3 indicates the composition of this fraction subdivided by group of compounds. As the composition of the products depends on the operating conditions, Table 3 specifies two distributions obtained at two different reaction temperatures.

TABLE 2

Selectivity after 146 hours at a conversion of 55%

| Product | Selectivity (weight %) |
|---|---|
| Hydrogen | 0.38 |
| Methane | 0.8 |
| Ethylene | 7.88 |
| Ethane | 0.78 |
| Propylene | 39.1 |
| Propane | 5.54 |
| C$_5^+$ | 45.52 |
| Total | 100.00 |

TABLE 3

Composition of the C$_5^+$ liquid fraction obtained with ZSM-12 (SiO$_2$/Al$_2$O$_3$ = 100 mol/mol) in weight %

| Reaction T (° C.) | BTX % | NAPHTHALENES % | C$_5^+$ (non aromatics) % | OTHERS % |
|---|---|---|---|---|
| 500 | 40 | 8 | 17.5 | 34.5 |
| 500 | 55 | 7 | 5.5 | 32.5 |

The term BTX refers to benzene, toluene and xylenes. The heading NAPHTHALENES comprises all hydrocarbons, variously substituted, of the naphthaline family. The term C$_5^+$ (non aromatics) refers to non aromatic hydrocarbons, saturated and mono-unsaturated, containing 5-8 carbon atoms. The term OTHERS comprises those products for which it was not possible to effect a gaschromatographic characterization It can be seen how among the by-products, there are large quantities of easily exploitable products such as BTX.

Comparative Example 4

ZSM-12 (SiO$_2$/Al$_2$O$_3$=250 mol/mol)

The catalytic testing of ZSM-12 zeolite having a molar ratio SiO$_2$/Al$_2$O$_3$=250, whose synthesis is described in example 2, was effected using the equipment described above and under the exact operating conditions specified in example 3.

Figure 2:
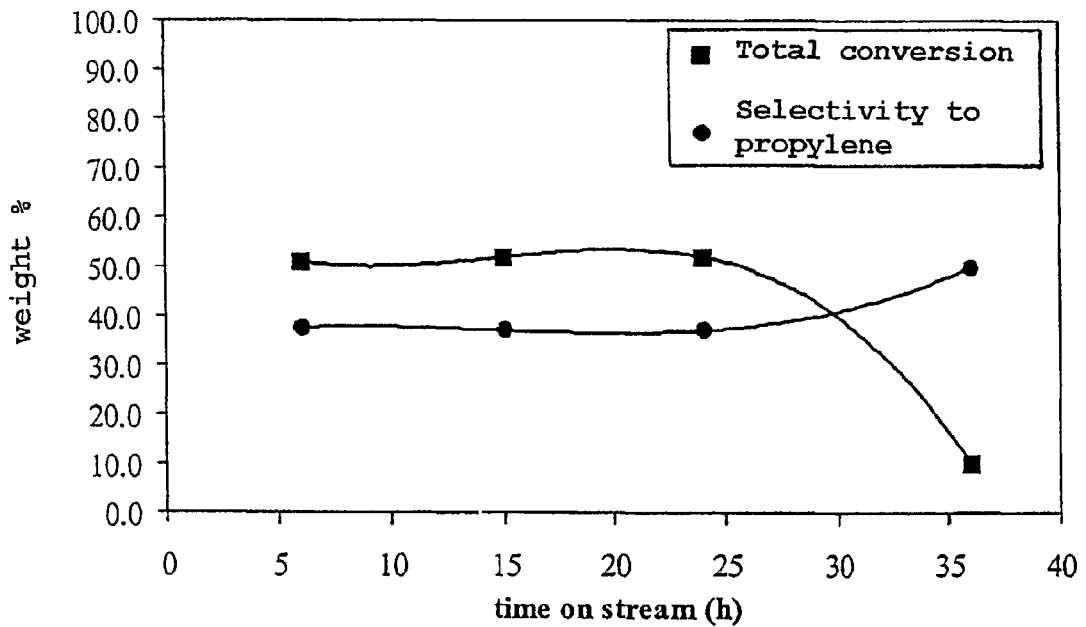

FIG. 2 indicates the two curves relating to total conversion and selectivity to propylene, obtained with this zeolite in relation to the time on stream (tos). The conversion and selectivity to propylene are defined as in example 3.

Contrary to what is specified in literature, the catalytic performances of ZSM-12 with a ratio SiO$_2$/Al$_2$O$_3$=250, are lower both in terms of yield (product of selectivity and conversion) and duration, with respect to the zeolite having a greater content of Al$_2$O$_3$.

It can be observed, in fact, from the graph of FIG. 2 how, already after 25 hours of tos, evident catalytic deterioration phenomena are present.

Table 5 indicates, for illustrative purposes, the selectivity of the various components forming the product at the plant outlet. Table 6, on the other hand, indicates the composition of the C$_5^+$ liquid fraction subdivided by group of compounds.

TABLE 5

Selectivity after 24 hours at a conversion of 52%

| Product | Selectivity (weight %) |
|---|---|
| Hydrogen | 0.4 |
| Methane | 0.6 |
| Ethylene | 4.41 |
| Ethane | 0.42 |
| Propylene | 37.0 |
| Propane | 3.82 |
| $C_5^+$ | 53.35 |
| Total | 100.00 |

TABLE 6

Composition in weight % of the $C_5^+$ liquid fraction obtained with ZSM-12 ($SiO_2/Al_2O_3$ = 250 mol/mol)

| Reaction T (° C.) | BTX % | NAPHTHALENES % | $C_5^+$ (non aromatics) % | OTHERS % |
|---|---|---|---|---|
| 500 | 35 | 3.5 | 17.5 | 44 |

The term BTX refers to benzene, toluene and xylenes; the heading NAPHTHALENES comprises all hydrocarbons, variously substituted, of the naphthaline family; the term $C_5^+$ (non aromatics) refers to non aromatic hydrocarbons, saturated and mono-unsaturated, containing 5–8 carbon atoms. The term OTHERS comprises those products for which it was not possible to effect a gaschromatographic characterization.

Comparative Example 5

Commercial ZSM-5

The catalytic testing of commercial ZSM-5 zeolite (CBV 3020 E) having a molar ratio $SiO_2/Al_2O_3$=30, was effected using the equipment described above and under the exact operating conditions described in example 3.

Figure 3:
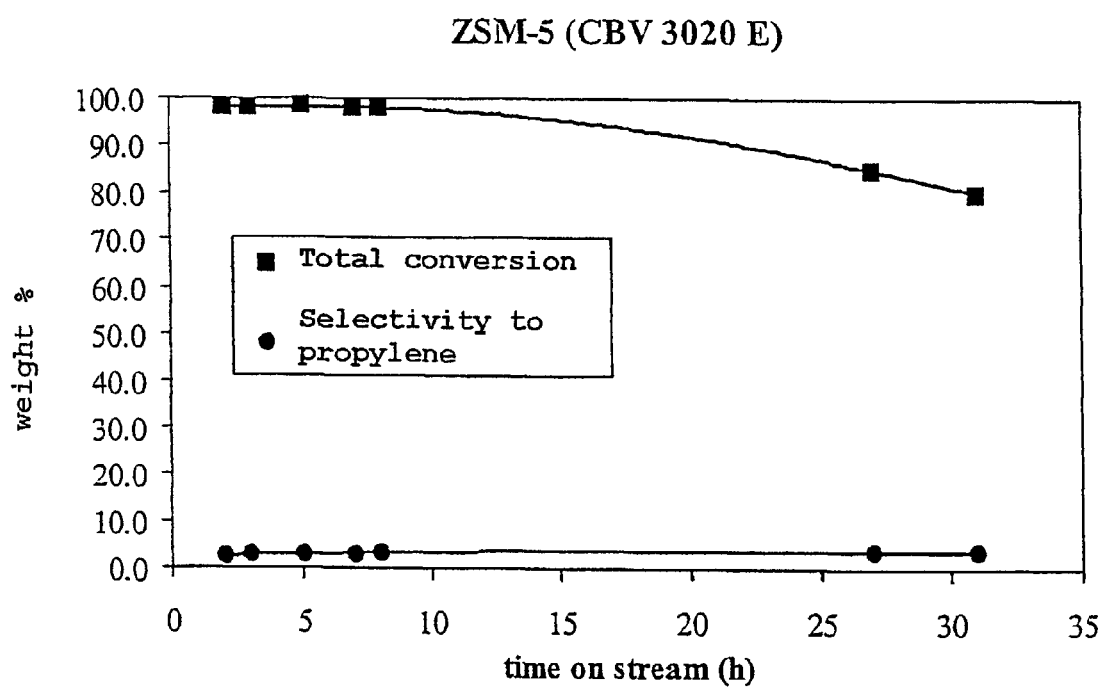

FIG. 3 indicates the two curves relating to total conversion and selectivity to propylene, obtained with this zeolite in relation to the time on stream (tos).

The conversion and selectivity to propylene are defined as in example 3.

The catalytic performances of ZSM-5 are much lower both in terms of yield (product of selectivity and conversion) and duration, with respect to the ZSM-12 zeolite.

It can be observed, in fact, from the graph of FIG. 3 how, already after 10 hours of tos, evident catalytic deterioration phenomena are present.

Table 7 indicates, for illustrative purposes, the selectivity of the various components forming the product at the plant outlet.

Table 8 specifies the composition of the $C_5^+$ fraction subdivided by group of compounds.

TABLE 7

Selectivity after 27 hours at a conversion of 85%

| Product | Selectivity (weight %) |
|---|---|
| Hydrogen | 1.63 |
| Methane | 3.70 |
| Ethylene | 3.03 |
| Ethane | 5.14 |
| Propylene | 3.84 |
| Propane | 34.15 |
| $C_5^+$ | 48.51 |
| Total | 100.00 |

TABLE 8

Composition in weight % of the $C_5^+$ liquid fraction obtained with commercial ZSM-5

| Reaction T (° C.) | BTX % | NAPHTHALENES % | $C_5^+$ (non aromatics) % | OTHERS % |
|---|---|---|---|---|
| 500 | 80 | — | — | 20 |

The invention claimed is:

1. A process for the production of propylene consisting of contacting a mixture of hydrocarbons with a catalyst composition under cracking conditions, thereby producing a product comprising propylene from said mixture,
   wherein the mixture of hydrocarbons comprises predominately olefins, the mixture has a boiling point ranging from −15° C. to +80° C., the catalyst composition comprises a large pore zeolite comprising a lattice of 12 tetrahedrons, and the zeolite has a molar ratio of silica/alumina from 100 to 200.

2. The process according to claim 1, wherein the mixture of hydrocarbons has a boiling point ranging from −12° C. to +60° C.

3. The process according to claim 1, wherein the zeolite is a ZSM-12 zeolite.

4. The process according to claim 3, wherein the ZSM-12 zeolite has a molar ratio silica/alumina ranging from 100 to 150.

5. The process according to claim 1, wherein the mixture of hydrocarbons comprises from 30% to 100% by weight of olefins.

6. The process according to claim 5, wherein the mixture of hydrocarbons has a content of 40% to 85% by weight of olefins.

7. The process according to claim 1, wherein the process is carried out at a temperature ranging from 400° C. to 750° C.

8. The process according to claim 7, wherein the temperature ranges from 450 °C. to 700 °C.

9. The process according to claim 8, wherein the temperature ranges from 500 °C. to 650 °C.

10. The process according to claim 1, wherein the process is carried out at a weight hourly space velocity (WHSV) ranging from 0.1 h$^{-1}$ to 1,000 h$^{-1}$.

11. The process according to claim 10, wherein the weight hourly space velocity ranges from 0.5 h$^{-1}$ to 100 h$^{-1}$.

12. The process according to claim 11, wherein the weight hourly space velocity ranges from 0.8 h$^{-1}$ to 50 h$^{-1}$.

13. The process according to claim 1, wherein the zeolite has a molar ratio of silica/alumina ranging from 150 to 200.

14. The process according to claim 1, wherein the zeolite has a molar ratio of silica/alumina of 100.

15. The process according to claim 1, wherein the catalyst composition maintains catalytic activity for 25 hours or more.

16. The process according to claim 1, wherein the catalyst composition maintains approximately the same level of conversion for 25 hours or more.

17. The process according to claim 1, wherein the catalyst composition maintains catalytic activity and maintains approximately the same level of conversion, both for 25 hours or more.

18. A process for the production of propylene consisting of contacting a mixture of hydrocarbons with a catalyst composition under cracking conditions, thereby producing a product comprising propylene from said mixture, wherein the mixture of hydrocarbons comprises predominately olefins, the mixture has a boiling point ranging from −15°°C. to +80° C., the catalyst composition comprises a large pore zeolite comprising a lattice of 12 tetrahedrons, and the zeolite has a molar ratio of silica/alumina less than 200; and wherein the zeolite is prepared by the steps comprising:

contacting sodium aluminate with an aqueous solution of tetramethyammonium hydroxide to form a mixture, contacting the mixture with colloidal silica to form a homogeneous gel, crystallizing the gel under hydrothermal conditions to obtain a first solid, washing the first solid with water to form a second solid, calcining the second solid in air to form a calcined solid, subjecting the calcined solid to an ion exchange using an aqueous solution of ammonium acetate to form a third solid, and calcining the third solid in air.

* * * * *